United States Patent [19]

Frigerio

[11] 4,263,272

[45] Apr. 21, 1981

[54] PHARMACEUTICAL COMPOSITION OF PROLONGED ACTION CONTAINING BILE ACIDS

[75] Inventor: Giuliano E. Frigerio, Bresso, Italy

[73] Assignee: Lehner AG, Muttenz, Switzerland

[21] Appl. No.: 103,108

[22] Filed: Dec. 13, 1979

[30] Foreign Application Priority Data

Dec. 15, 1978 [IT] Italy .............................. 30933 A/78

[51] Int. Cl.³ .......................... A61K 9/22; A61K 9/24; A61K 9/26; A61K 31/575
[52] U.S. Cl. ........................................ 424/19; 424/20; 424/21; 424/22; 424/238
[58] Field of Search .................................... 424/19–22, 424/32–38, 238

[56] References Cited

U.S. PATENT DOCUMENTS

| | | | |
|---|---|---|---|
| 3,574,819 | 4/1971 | Gross et al. | 424/21 |
| 3,651,205 | 3/1972 | Hunger et al. | 424/21 |
| 3,839,565 | 10/1974 | Saltzman | 424/238 |
| 3,852,440 | 12/1974 | Weigand | 424/238 |
| 3,859,437 | 1/1975 | Weigand | 424/238 |

OTHER PUBLICATIONS

Robinson Sustained Action Dosage Forms, Ch. 14, pp. 439–465 of Lachman et al., Ed. Theory & Practice of Industrial Pharmacy, 2nd Ed. (1976) Lea & Febig, Phila., Pa.

Ballard et al. Prolonged Action Pharmaceuticals, Ch. 89, pp. 1699–1714, 1726–1728 of Remington's Pharmaceutical Sciences, 14th Ed. (1970) Mack Pub. Co., Easton, Pa.

*Primary Examiner*—Shep K. Rose
*Attorney, Agent, or Firm*—Cushman, Darby & Cushman

[57] ABSTRACT

The present invention relates to a composition for oral use containing a bile acid as active principle, particularly suitable for the lysis of calculi of cholesterol origin, characterized in that it is in such a form as to yield up its active principle over a prolonged time period and is administered in a daily dose to be consumed in one taking.

22 Claims, No Drawings

PHARMACEUTICAL COMPOSITION OF PROLONGED ACTION CONTAINING BILE ACIDS

The administration of bile acids for the purpose of desaturating lithogenous bile supersaturated with cholesterol and to consequently obtain the lysis of already formed cholesterol calculi is of recent introduction in the human therapy field.

It is however important to note that the therapy based on such drugs requires long periods of treatment, for example between six months and two years, and the regular and correct taking of the drug is one of the essential factors for the proper success of the therapy. In this respect, a patient with calculi is often asymptomatic in that he suffers no dispepsia or pain, one reason for this being the rapid effect of the treatment. He is also mostly in a state of full working activity, and therefore as he suffers no particular stimuli he is easily induced, either by forgetfulness or neglect, to omit the daily administration, thus nullifying the effectiveness of a long, costly and demanding treatment cycle.

In this respect, in the case for example of ursodeoxycholic acid, the effective therapeutic dose at present used in the art is 8–10 mg/kg die, corresponding on average to one daily dose of 600–750 mg/die for a normal adult.

Such a quantity of active substance is at the present time administered in the form of individual doses split over the 24 hours, generally 3–5 capsules/die of dose units, each equal to about 150 mg of bile acid.

The pharmacodynamically active dose of the known art for a further two important bile acids are as follows: chenodeoxycholic acid or CDCA, approximately 15 mg/kg die, equal to approximately 1.1 g/die for a normal adult; 7-α-ketolithocholic acid 10–15 mg/kg die, equal to approximately 0.6–1 g/die for a normal adult.

The aforesaid administration gives rise to different effects, for equal total daily doses, according to the frequency of the administrations and their distribution during the day. This for example has been clearly shown by Northfield & Coll. (5th Bile Acid Meeting, Freiburg 12–14 June 1978) for chenodeoxycholic acid. A single evening administration was clinically more effective than administrations regularly distributed to coincide with meals.

These differences of effect are obviously related to the facility for ensuring selective distribution of the pharmacological "cover" in the antilithogenic sense during those periods of the day in which the bile tends to become concentrated at the cholecystic level with an increase in cholesterol saturation and the facility for precipitating crystals and forming calculi. These periods coincide mainly with the fasting periods during the day. Evening administration would ensure a greater effect by giving a more rational cover of the most critical period.

On the other hand, it must be considered that that which is valid for Anglo Saxon peoples is not valid for Latin peoples because of the different eating habits. In this respect, Latin peoples generally prolong the night fasting period through the morning as their breakfast is very light and free from fats or eggs, or indeed absent.

This would suggest that the time span for "pharmacological cover" should be about twelve hours.

The optimum method would obviously require an exact knowledge of the individual biorhythm of the bile production and of the composition variations during the day. As it is impossible to carry out individual determinations with such precision, on the one hand recourse must be made to basic physiopathological knowledge, and on the other hand the gradients of effectiveness of the different comparative technico-pharmaceutical solutions must be verified. Although comparisons in terms of bioavailability of the active principle are important from the knowledge aspect and as a verification of the validity of the techniques, they do not however seem exhaustive at a practical level in that they do not provide data on the time concomitance between maximum effect and maximum requirement.

A first object of the present invention is therefore to optimise the therapeutic effectiveness of preparations of the described type based on bile acids, by making the taking of the drug extremely simple and schematic by means of a single daily administration at bedtime.

Further objects of the present invention are as follows:

to provide an effectiveness which is at least equivalent or indeed greater than that of the known art using doses substantially less than the doses of the known art given in multiple administration, in order to obtain optimum cover during the phases of major bile supersaturation;

to reduce the cost of therapy, which is particularly high due to the high cost of the raw material and the long duration of treatment;

to reduce the probability of side-effects occurring by reducing the pharmacological "load."

The present invention obviates the aforesaid problems of the known art and attains the aforesaid objects by a pharmaceutical composition for oral use containing a bile acid as its active principle, and particularly suitable for the lysis of calculi of cholesterol origin, which is in such a form as to yield up its active principle over a protracted time period and is administered in a daily dose to be consumed in one taking.

The bile acids mainly used according to the invention are ursodeoxycholic acid, chenodeoxycholic acid and 7-α-ketolithocholic acid.

The structural formula of ursodeoxycholic acid, or 3α7β-dihydroxy-5β-cholanic acid, indicated by UDCA for brevity, is given hereinafter.

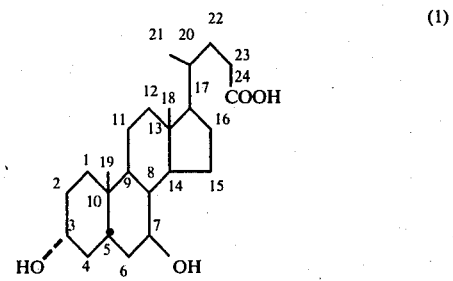

(1) This is the epimer of chenodeoxycholic acid or CDCA with respect to the hydroxyl in position 7.

7-α-ketolithocholic acid has the following structural formula:

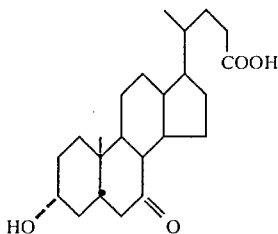
(2)

In a secondary capacity, the invention also provides for the use of other bile acids derived from cholic acid, substantially similar to the three stated heretofore.

Said single-dose pharmaceutical composition is preferably administered at bedtime. Said time-protracted yielding up of the active principle can be attained in accordance with one of the two following forms:

gradual release and absorption over a minimum of 8 and a maximum of 12 hours.

release and absorption over two or more stages, of which the first takes place immediately on administration, and the second or remaining stages take place over the subsequent time period at substantially regular intervals in order to give cover as far as the twelfth hour.

A preferred form of the pharmaceutical composition according to the invention comprises a dose unit of 450–500 mg, which is particularly valid for ursodeoxycholic acid.

A further form of the composition can comprise a dose unit of 600 mg.

In the case of chenodeoxycholic acid, which as stated is effective at greater doses than its UDCA epimer, a dose unit of this latter type is preferably provided, possibly administered in two successive administration units, for example tablets, in order for the unit to be of such a size as to allow easy swallowing.

In order to more fully describe the characteristics of the pharmaceutical compositions according to the present invention, some embodiments are described hereinafter, preceded by a short consideration of the various techniques relative to the possible models for the yielding-up of the active principle of said pharmaceutical compositions.

The compositions of said examples relate in particular to ursodeoxycholic acid, indicated by the abbreviation UDCA. However, compositions according to the invention based on other bile acids, in particular the two remaining acids stated heretofore, are completely homologous to those indicated in the examples given hereinafter, which must therefore not be considered as limiting the scope of the invention.

Definition of the base unit:

To simplify the descriptive survey of the method models for the yielding up of the active principle given hereinafter, it is considered useful to define the term "base unit," which is meant generally to mean any single-dose oral pharmaceutical form, for example a tablet, containing the minimum therapeutic dose able to make available to the organism a quantity of drug considered sufficient to give the desired pharmacological response as rapidly as is in accordance with those properties of the drum which determine its intrinsic availability for absorption (Casadio Vol. I page 892).

Scheme of the method models for the yielding up of the active principle:

(1) Model comprising repeated action dependent on the attacking fluids.
  (a) with compact base unit
  (b) with subdivided base unit
(2) Model comprising repeated action independent of the attacking fluids.
(3) Model comprising sustained or protracted action
  (a) with yielding-up of the active principle uniformly divided
  (b) with yielding-up of the active principle divided but with negative gradient
  (c) with compound yielding-up of the active principle.

Model comprising repeated action dependent on the attacking fluids

Fundamental characteristics: this provides two or more base units, each sequentially available for absorption into a more or less defined tract of the gastroenteric duct, characterised by particular chemical-physical conditions (e.g.: pH, digestive enzymes etc.). Generally one of the base units is made immediately available for absorption, compatible with its intrinsic characteristics.

It is important to distinguish between two quite different types:

(a) Compact base unit type

Specific characteristics: this is characterised by the fact that each protective base unit is coated in a single portion over the entire exposed surface. It allows good repeatability of the dose in the required sites, but due mainly to the variability of the times of emptying the stomach it can lead to repetition of the action in too rapid succession (see Casadio Vol. I, page 891).

Practical formation: the model is formed by combining a number "n" of identical or similar base units by various methods, and of which all or "n-1" are protected from contact with the gastrointestinal juices by substances which are of varying sensitivity to particular properties of the attacking medium, using various methods. The combination can be in parallel (e.g. gelatine capsules containing two or more tablets), or in series (e.g. tablets or pills comprising concentric sectors), in which case the sequence of base units must present itself to the attacking fluids in a sequence identical to that of the yield-up sites.

EXAMPLE 1 a

Pill of repeated action comprising two base units with immediate disgregation (stomach) and disgregation at pH≧7 (inferior small intestine-colon) respectively.

Description of the pharmaceutical form: varnished pill comprising concentric coated sectors.

Principle of the practical model: this is based on the use of known filmogenic materials which form coatings which are soluble at different pH values according to the type used.

| Description | Constituent elements of the pharmaceutical form | | Technology used |
| --- | --- | --- | --- |
| | Components | | |
| 1. Internal nucleus: Base unit for retarded disgregation | UDCA | 100 | This is obtained by compressing a granulate prepared by a dry compacting |
| | Starch Microgranular | 6 | |

-continued

| Description | Components | | Technology used |
|---|---|---|---|
| | cellulose | 12 | process |
| | Casein formaldehyde | 4 | |
| | Mg stearate | 2 | |
| 2. 1st layer: Protective coating soluble at pH≧7 | Eudragit S.12.5P (dry matter) | 16 | This is applied in a coating pan by a spray process |
| 3. 2nd layer: Base unit for immediate disgregation | UDCA | 100 | This is applied in a coating pan by a spray process. The components are carried in solution or suspension with ethyl alcohol |
| | Polyvinylpyrrolidone | 20 | |
| | Polyethyleneglycol 6000 | 12 | |
| | Starch | 16 | |
| | Carboxymethyl-cellulose mv | 8 | |
| 4. Peripheral layer: Finishing coating soluble at pH<5 | Eudragit E 12.5 (dry matter) | 4 | This is applied in a coating pan by a spray process. The components are carried in solution or suspension with the fluid varnish EUDRAGIT E 12.5 |
| | Talc | 2 | |
| | Titanium dioxide | 1 | |
| | Colorant E 172 | 0.008 | |
| | Alumina | 0.032 | |
| | Polyethyleneglycol 6000 | 0.4 | |

"In vitro" verification of the model:

Pills were investigated "in vitro" by the USP XIX method, modified in the composition and sequence of the simulated gastrointestinal fluids, and gave the following results after one hour (pH 1.5):

peripheral layer + 2nd layer completely disgregated. No substantial change in the lower sectors between 2 and 6 hours (pH 4.5–6.9), no further disgregation;

after 7 hours (pH 7.2): internal nucleus completely disgregated.

EXAMPLE 2a

Gelatine capsule of repeated action comprising three base units with disgregation immediate (stomach), at pH≧6 (lower intestine) and at pH≧7 (inferior lower intestine-colon) respectively. Description of the pharmaceutical form: hard gelatine capsule containing three tablets with different coatings and colouration. Principle of the practical model: this is based on the use of known filmogenic materials which form coatings solube at different pH values according to the type used.

| Description | Components | | Technology used |
|---|---|---|---|
| 1. Tablets: Base unit designed for successive diversification by means of the coatings listed below | UDCA | 100 | This is obtained by compressing a granulate prepared by a dry compacting process |
| | Starch | 6 | |
| | Microgranular cellulose | 12 | |
| | Casein formaldehyde | 4 | |
| | Mg stearate | 2 | |
| 2. Coating A: Protective film soluble at pH<5 | Eudragit E 12.5 (dry matter) | 6 | This is applied, on one third of the previously prepared tablets, in a coating pan by a spray process. The components are carried in solution or suspension with the fluid varnish EUDRAGIT E 12.5 |
| | Talc | 3 | |
| | Titanium dioxide | 1.5 | |
| | Polyethyleneglycol 6000 | 0.6 | |
| 3. Coating B: Protective film of mixed lattice with a portion soluble at pH≧6, together with an insoluble portion | Eudragit L 12.5P (dry matter) | 12 | This is applied, on one third of the previously prepared tablets, in a coating pan by a spray process. The components are carried in solution or suspension with the mixture of fluid varnishes EUDRAGIT L 12.5P and RS 12.5 |
| | Eudragit ES 12.5 (dry matter) | 6 | |
| | Talc | 6 | |
| | Titanium dioxide | 3 | |
| | Colorant E 172 | 0.024 | |
| | Alumina | 0.096 | |
| | Polyethyleneglycol 6000 | 1.2 | |
| 4. Coating C: Protective film of mixed lattice with a portion soluble at pH≧7, together with an insoluble portion | Eudragit S 12.5P (dry matter) | 12 | This is applied, on one third of the previously prepared tablets, in a coating pan by a spray process. The components are carried in solution or suspension with the mixture of fluid varnishes EUDRAGIT S 12.5P and RS 12.5 |
| | Eudragit RS (dry matter) | 6 | |
| | Talc | 6 | |
| | Titanium dioxide | 3 | |
| | Colorant E 172 | 0.072 | |
| | Alumina | 0.288 | |
| | Polyethyleneglycol 6000 | 1.2 | |
| 5. Gelatine casing: The purpose of this is simply to act as a gastro-soluble container in order to assemble the three varnished tablets into a single dose (N.B. In case of swallowing difficulties, the tablets can be | Hard gelatine capsules, self-locking, size 00 | | The tablets are encapsulated by means of an automatic encapsulating machine fitted with a tablet dispenser. As self-locking capsules are used, the capsules can be opened to |

| Description | Components | Technology used |
|---|---|---|
| removed from the casing and swallowed one at a time) | | give easy access to the individual tablets should the need indicated in the description arise |

"In vitro" verification of the model:

The disgregation of the capsules was investigated "in vitro" using the USP XIX method, modified in terms of the composition and sequence of the simulated gastrointestinal fluids, and the following results were obtained:

after 1 hour (pH 1.5): complete disgregation of the gelatine casing and of the tablets with coating A. No substantial alteration in the tablets with coating B or C.

from 2 to 3 hours (pH 4.5–6.9): no further substantial alteration after 4 hours (pH 6.9): complete disgregation of tablets with coating B from 5 to 7 hours (6.9–7.2): no further substantial alteration after 8 hours (pH 7.2): all tablets were completely disgregatated.

(b) Subdivided base unit type

Specific characteristics: this is characterised by the fact that the base unit is constituted by an assembly of a considerable number of sub-units designed to be independent in terms of their speed of transfer into the gastroenteric duct.

For probability reasons, this tends to compensate the variations in transfer times by avoiding action repetitions which are too close in time (see Casadio Vol. I page 891), but decreases the accuracy of dose reproducibility.

Practical formation: the model is formed by combining by various methods a number "n" of base units each constituted by a considerable number of sub-units which are more or less rigidly joined together.

The sub-units relative to all or to n−1 base units are individually protected, by various methods, with a coating of substances of different sensitivities to particular properties of the attacking medium, which is the same for each base unit but is different between one unit and the others.

The combination can be in parallel (e.g.: gelatine capsules containing a mixture of chronoids); in series (tablets or pills in the form of concentric sectors), in which case the sequence of base units must present itself to the attacking fluids in a sequence identical to that of the yield-up sites; or of mixed form (e.g. multi-layer tablets, mixed granule tablets).

EXAMPLE 1b

Gelatine capsules of repeated action comprising two subdivided base units, with disgregation which is immediate (stomach) and at pH≧7 (inferior small intestine-colon) respectively.

Description of the pharmaceutical form: hard gelatine capsule containing, in identical quantities, two types of microtablet each differently coated and coloured.

Principle of the practical model: this is based on the use of known filmogenic materials which form coatings soluble at different pH values according to the type used.

| Description | Components | | Technology used |
|---|---|---|---|
| 1. Normal microtablets: Base unit of immediate disgregation | UDCA | 100 | This is obtained by compressing a granulate prepared by a dry compacting process. The coating is applied in a coating pan by a spray process |
| | Starch | 6 | |
| | Microgranular cellulose | 12 | |
| | Casein formaldehyde | 4 | |
| | Mg stearate | 2 | |
| | Eudragit E 12.5 (dry matter) | 8 | |
| 2. Protected microtablets: Base unit for retarded disgregation | UDCA | 100 | This is obtained by compressing a granulate prepared by a dry compacting process. The coating is applied in a coating pan by a spray process |
| | Starch | 6 | |
| | Microgranular cellulose | 12 | |
| | Cesein formaldehyde | 4 | |
| | Mg stearate | 2 | |
| | Eudragit S 12.5P (dry matter) | 30 | |
| | Colorant E 127 (dry matter) | 0.010 | |
| | Alumina | 0.040 | |
| 3. Gelatine casing: The purpose of this is simply to act as a gastro-soluble container for assembling the coated microtablets into individual doses | Hard gelatine capsules, self-locking, size 00 | | The coated microtablets are assembled in hard gelatine capsules by an automatic encapuslating machine fitted with a microtablet dispensing unit |

"In vitro" verification of the practical model:

The disgregation of the capsules was investigated "in vitro" by the USP XIX method, modified in the composition and sequence of the simulated gastrointestinal fluids, and gave the following results:

after 1 hour (pH 1.5): complete disgregation of the gelatine casing and of the non-coloured microtablets. No alteration of the coloured microtablets (also checked by weight)

from 2 to 6 hours (pH 4.5–6.9): no further disgregation after 7 hours (pH 7.2): coloured microtablets completely disgregated.

Model comprising repeated action independent of the attacking fluids

Fundamental characteristics: this provides two or more base units, each sequentially available for absorption at predetermined time intervals and, compatibly with its intrinsic characteristics, substantially independent of the variation in the environment encountered during gastrointestinal transit. Generally one of the base units is immediately available for absorption, as far as is compatible with its intrinsic characteristics. It is considered of little importance to identify further sub-classes, as the accurate reproduction of the proposed theoretical model is related to exclusively technological factors, whatever the practical model which is to be formed. Practical formation: the model is formed by combining a number "n" of identical or similar base units by various methods, and of which all or "n−1" are variously protected, by known methods, from contact with the gastrointestinal juices by substances which are influenced only or mainly by one or more factors which remain substantially identical along the entire gastrointestinal tract.

The combination can be in parallel (e.g. gelatine capsules containing two or more tablets), or in series (e.g. tablets or pills comprising concentric sectors), in which case the sequence of base units must present itself to the attacking fluids in a sequence identical to that of the yield-up sites.

EXAMPLE 1

Pill of repeated action comprising two base units with immediate disgregation and disgregation after 6 hours respectively.

Description of the pharmaceutical form: pill comprising coated concentric sectors.

Principle of the practical model: a tablet is formed in which the poorly water-soluble active principle is intimately mixed with a water swelling substance. The tablet is coated with a relatively elastic semipermeable film of low permeability. The resistance of the coating to the internal bursting pressure exerted by the cooperating substance, which becomes swollen by the water penetrating into the protected nucleus by osmosis, determines the time of rupture of the coating, with consequent direct exposure of the contents to the attacking fluids. Immediate yield-up is obviously attained by using a non-protected active principle.

| Description | Constituent elements of the pharmaceutical form | | Technology used |
|---|---|---|---|
| | Components | | |
| 1. Tablet: Base unit of delayed disgregation | UDCA | 100 | This is obtained by compressing a granulate prepared by dry compacting of the components |
| | Starch | 2 | |
| | Microgranular cellulose | 12 | |
| | Casein formaldehyde | 4 | |
| | Carboxymethylcellulose mv | 4 | |
| | Mg stearate | 2 | |
| 2. 1st layer: Semipermeable protective layer | Eudragit RS 12.5 (dry matter) | 12 | This is applied in a coating pan by a spray process |
| 3. 2nd layer: Base unit for immediate disgregation | UDCA | 100 | This is applied in a coating pan by a spray process. The components are carried in solution or suspension with ethyl alcohol |
| | Polyvinylpyrrolidone | 20 | |
| | Polyethyleneglycol 6000 | 12 | |
| | Starch | 16 | |
| | Carboxymethylcellulose mv | 8 | |
| 4. Peripheral layer: gastrosoluble finishing coating | Eudragit E 12.5 (dry matter) | 4 | This is applied in a coating pan by a spray process. The components are carried in solution or suspension with the fluid varnish EUDRAGIT E 12.5 |
| | Talc | 2 | |
| | Titanium dioxide | 1 | |
| | Colorant E 172 | 0.008 | |
| | Alumina | 0.032 | |
| | Polyethyleneglycol 6000 | 0.4 | |

"In vitro" verification of conformity to the theoretical model

The tablets were investigated "in vitro" by the USP XIX method, modified in the composition and sequence of the simulated gastrointestinal fluids, and gave the following results:

after 1 hour (pH 1.5): peripheral layer and 2nd layer completely disgregated; no substantial alteration to the lower sectors from 2 to 6 hours (pH 4.5–6.9): no further disgregation after 7 hours (pH 7.2): internal nucleus completely disgregated.

Model comprising sustained or protracted action

Fundamental characteristics: this provides one base unit immediately available for absorption, as compatible with its intrinsic characteristics, followed by various fractions of a base unit so as to maintain the activity of the drug as constant as possible during a predetermined time period, in addition to that due to the habitual single dose, i.e. to the base unit itself. A description of any sub-classes is considered to be of secondary importance as the main concept on which each possible variation is based, whatever the basic technology and special arrangements used, is to mainly obtain an "in vitro" absorption dissolution or yield-up curve for the drug which is rigorously repeatable and is as independent as possible of variations in the attacking fluids.

However, when the human pharmacokinetic data are not well known, it is considered advisable to present for "in vitro" investigation at least three different types of models comprising protracted yielding-up of the active principle, namely:

(a) in total dose with yielding-up of the active principle uniformly divided over the required time (b) in total dose with a negative yield-up gradient of the active principle (c) in total dose composed of a fraction of immediate yielding-up of the active principle, and a fraction in which the active principle is yielded up uniformly with time.

Even when a practical model is able to be formed which faithfully reproduces the ideal "in vitro" active principle yield-up curve for the drug, assuming that it is possible to predetermine it, it is generally necessary to submit to "in vivo" investigation various technological forms of the same model in order to have prior knowledge of any possible "vitro/vivo" divergencies. Practical formation: the model is formed by various methods, which enable either a quantitatively uniform or differential gradual and reproducible yielding-up of the active principle to the gastrointestinal juices to be obtained for the drug in its pharmaceutical form.

EXAMPLE 2

Gelatine capsules of the drug in which the active principle is yielded up in a manner uniformly distributed over a period of 10 hours.

Description of the pharmaceutical form: hard gelatine capsules containing microencapsulated granules.

Principle of the practical method: the gradual yielding-up of the active principle is obtained by microencapsulating the active substance in coacervations of gelatine which are then hardened to various degrees and in different quantities with formaldehyde in order to obtain varying degrees of hydrolysis of the gelatine.

| Constituent elements of the pharmaceutical form | | | | |
|---|---|---|---|---|
| Description | Components | | | Technology used |
| 1. Microencapsulated granules: | UDCA | 100 | | NCR patented process |
| Granules of the active principle individually coated with gelatine hardened to different degrees and in different quantities | Gelatine | 17 | | |
| | Precipitated silica | 5 | | |
| | Formaldehyde | traces | | |
| 2. Gelatine casing: The purpose of this is simply to act as a gastrosoluble container for distributing the microencapsulated granules into individual doses | Hard gelatine capsules, self-locking, size 00 | | | The microencapsulated granules are distributed into hard gelatine capsules by an automatic encapsulating machine fitted with a dispensing unit for slidable granules |

"In vitro" verification of the practical model:

The microencapsulated granules without their gelatine casing were subjected to "in vitro" investigation of the yielding-up of their active principle by the rotating flask method using the EURAND apparatus, and gave the following results:

| Time | pH | % Yielded up |
|---|---|---|
| 1 | 6.9 | 9 |
| 2 | 6.9 | 10.5 |
| 3 | 6.9 | 10 |
| 4 | 6.9 | 9.5 |
| 5 | 7.2 | 11 |
| 6 | 7.2 | 11 |
| 7 | 7.2 | 9.5 |
| 8 | 7.2 | 11.5 |
| 9 | 7.2 | 10 |
| 10 | 7.2 | 7.5 |

EXAMPLE 3

Insoluble matrix-type tablet which gradually yields up the active principle, with a negative gradient, over a period of 10 hours.

Description of the pharmaceutical form: tablets with insoluble excipients.

Principle of the practical model: the gradual yielding-up of the active principle is obtained by reducing the interface of the drug granules in contact with the gastrointestinal fluids by incorporating them into an insoluble matrix.

The negative gradient is obtained automatically by the gradual reduction in the contact area, with the simultaneous increase in the difficulty of penetration of the attackinfluids.

| Constituent elements of the pharmaceutical form | | | |
|---|---|---|---|
| Description | Components | | Technology used |
| Insoluble matrix-type tablet | UDCA | 100 | This is obtained by |
| | Calcium phosphate | 195 | compressing a mixture of |
| | Sodium lauryl sulphate | 3 | two granulates prepared by |
| | Mg stearate | 2 | a dry compacting method |

"In vitro" verification of the practical model:

The tablet was subjected to "in vitro" investigation of the yielding-up of its active principle by the USP XIX method, modified in the composition and sequence of the gastrointestinal fluids, and gave the following results:

| Time | pH | % yielded up |
|---|---|---|
| 1h | 6.9 | 21 |
| 2h | 6.9 | 18.5 |
| 3h | 6.9 | 17.5 |
| 4h | 6.9 | 15 |
| 5h | 6.9 | 10.5 |
| 6h | 7.2 | 7 |
| 7h | 7.2 | 4.5 |
| 8h | 7.2 | 2.5 |
| 9h | 7.2 | 1.5 |
| 10h | 7.2 | 0.5 |

EXAMPLE 4

Double layer tablet comprising one base unit of immediate disgregation plus one special unit of gradual uniform yield-up of its active principle over the period between 2 and 11 hours.

Description of the pharmaceutical form: tablet in the form of two layers, one of which is prepared from non-protected granules, and the other from granules with a permeable coating.

Principle of the active model: in addition to the non-protected active principle which is obviously yielded up immediately, there is also gradual yield-up due to diffusion through a permeable coating provided on a small fraction (granules) to prevent any substantial negative gradient effects, and made porous by making a portion of the coating reticulated in order to compensate for the low solubility of the active principle.

| | Constituent elements of the pharmaceutical form | | |
|---|---|---|---|
| Description | Components | | Technology used |
| 1. 1st layer: Non-protected base unit | UDCA | 100 | This is obtained by adding lubricant to a granulate prepared by a fluidised bed process, then lightly compressing. The first layer is then rigidly joined to the second by heavier compression |
| | Sorbitol | 9 | |
| | Gelatine | 10 | |
| | Mg stearate | 1 | |
| 2. 2nd layer: Special unit which gradually yields up its active principle | UDCA | 400 | This is obtained by adding lubricant to a granulate prepared by a fluidised bed process and coated by the same process, then lightly compressing. The second layer is rigidly joined to the first by heavier compression |
| | Sorbitol | 36 | |
| | Gelatine | 40 | |
| | Mg stearate | 4 | |
| | Eudragit RS 12.5 (dry matter) | 32 | |
| | Eudragit E 12.5 (dry matter) | 16 | |
| | Triacetin | 0.3 | |

"In vitro" verification of the practical model:

The tablet was subjected to "in vitro" investigation of the yielding-up of its active principle by the USP XIX method modified in the composition and sequence of the simulated fluids, and gave the following results:

| Time | pH | % yielding-up |
|---|---|---|
| 1 | 6.9 | 19 |
| 2 | 6.9 | 7 |
| 3 | 6.9 | 9 |
| 4 | 6.9 | 8.5 |
| 5 | 7.2 | 8.5 |
| 6 | 7.2 | 8.5 |
| 7 | 7.2 | 7 |
| 8 | 7.2 | 7 |
| 9 | 7.2 | 8 |
| 10 | 7.2 | 9 |
| 11 | 7.2 | 7.5 |

The various technical formulations formed in accordance with the aforegoing description gave surprisingly satisfactory results both in relation to the bioavailability rhythm of the active principle which was characteristic of the preparations and was studied by clinical tests carried out with the marked substance, and in relation to the effects of desaturation of the lithogenous bile encountered after one to two months of treatment and compared with the full dosages of the conventional preparations.

Summarising, it can be stated that the new formulations give at least equal effectiveness with effective doses which are less than those of the known art by at least about 20%. In the case of the 600 mg unit dose according to the invention, which is an amount substantially similar to the effective dose of the known art, there is the advantage of greater treatment effectiveness, but obviously not of a lesser cost of therapy.

Furthermore, by means of only one daily administration, these new formulations provide a pharmaceutical cover of at least 10 hours and up to 12 hours, and in some cases longer, so amply covering the period of greatest lithogenic risk, which coincides with the period between meals.

The practical aspect of the administration is advantageous in that it ensures that the therapy cycles will be regular, and thus eliminates an important negative variable of the known art.

Finally, the pharmaceutical compositions according to the present invention have proved highly active at the described daily doses of 450-500 mg/die, including in the hypertriglyceridemia therapy field.

I claim:

1. A pharmaceutical composition for oral use containing a bile acid as active principles adapted to lyse calculi of cholesterol origin, characterized by containing excipients which allow the active principle to be released over a protracted time period and, said active principle being present in an amount of 450-500 mg, said amount being the therapeutic daily dose, to be consumed in one taking.

2. A composition as claimed in claim 1, wherein said bile acid is ursodeoxycholic acid.

3. A composition as claimed in claim 1, wherein said bile acid is chenodeoxycholic acid.

4. A composition as claimed in claim 1, wherein said bile acid is 7-$\alpha$-ketolithocholic acid.

5. A composition as claimed in claim 2, wherein said composition is in the form of a single administration unit.

6. A composition as claimed in claim 3, wherein said composition is made up subdivided into two administration units which are equivalent to each other.

7. A composition as claimed in claim 4, which is administered in one unit or in two successive units respectively.

8. A composition as claimed in claim 1, wherein said protracted yielding-up of the active principle in time is of the gradual release and absorption, or sustained action type.

9. A composition as claimed in claim 1, wherein said protracted yielding-up of the active principle in time is of the repeated action release and absorption type, in two or more stages.

10. A composition as claimed in claim 7, wherein said yielding-up of the active principle takes place over a time of between 8 and 12 hours.

11. A composition as claimed in claim 8, wherein said yielding-up of the active principle takes place at successive times at substantially regular intervals until the twelfth hour from the time of administration.

12. A process for the lysis of calculi of cholesterol origin comprising administering to a patient with such calculi the pharmaceutical composition of claim 1.

13. A process as claimed in claim 12, wherein the bile acid is ursodeoxycholic acid.

14. A process as claimed in claim 13, wherein the composition is administered in the form of a single administration unit.

15. A process as claimed in claim 12, wherein the bile acid is chenodeoxycholic acid.

16. A process as claimed in claim 15, wherein the composition is administered in two administration units which are equivalent to each other.

17. A process as claimed in claim 12, wherein the acid is 7-α-ketolithocholic acid.

18. A process as claimed in claim 17, wherein the composition is administered in one unit or in two successive units.

19. A process as claimed in claim 18, wherein said yielding-up of the active principle takes place over a time of between 8 and 12 hours.

20. A process as claimed in claim 12, wherein said protracted yielding-up of the active principle in time is of the gradual release and absorption, or sustained action type.

21. A process as claimed in claim 20, wherein said yielding-up of the active principle takes place at successive times at substantially regular intervals until the twelfth hour from the time of administration.

22. A process as claimed in claim 12, wherein said protracted yielding-up of the active principle in time is of the repeated action release and absorption type, in at least two stages.

* * * * *